(12) United States Patent
Geesbreght et al.

(10) Patent No.: US 10,045,666 B2
(45) Date of Patent: Aug. 14, 2018

(54) HAND SANITIZING DEVICE AND METHOD OF USE

(71) Applicants: John M. Geesbreght, Fort Worth, TX (US); Darrell D. Dial, Fort Worth, TX (US)

(72) Inventors: John M. Geesbreght, Fort Worth, TX (US); Darrell D. Dial, Fort Worth, TX (US)

(*) Notice: Subject to any disclaimer, the term of this patent is extended or adjusted under 35 U.S.C. 154(b) by 0 days.

(21) Appl. No.: 15/606,949

(22) Filed: May 26, 2017

(65) Prior Publication Data

US 2017/0258275 A1 Sep. 14, 2017

Related U.S. Application Data

(60) Division of application No. 14/292,995, filed on Jun. 2, 2014, which is a continuation-in-part of application No. 12/788,887, filed on May 27, 2010, now Pat. No. 8,747,008.

(60) Provisional application No. 61/181,724, filed on May 28, 2009.

(51) Int. Cl.
| | |
|---|---|
| *A47K 5/12* | (2006.01) |
| *A61L 2/00* | (2006.01) |
| *A45D 34/04* | (2006.01) |
| *A45F 5/02* | (2006.01) |
| *A45D 34/00* | (2006.01) |

(52) U.S. Cl.
CPC ............... *A47K 5/12* (2013.01); *A45D 34/00* (2013.01); *A45D 34/041* (2013.01); *A45F 5/021* (2013.01); *A47K 5/1201* (2013.01); *A61L 2/0088* (2013.01)

(58) Field of Classification Search
CPC ......... A45F 5/021; A47K 5/12; A47K 5/1201; A61M 35/00; A61M 35/003
USPC .................................................. 401/8, 188 R
See application file for complete search history.

(56) References Cited

U.S. PATENT DOCUMENTS

| | | | | |
|---|---|---|---|---|
| 962,682 | A * | 6/1910 | Wade | A47K 5/12 |
| | | | | 222/341 |
| 1,819,382 | A * | 8/1931 | Palmer | A47K 5/12 |
| | | | | 222/181.2 |
| 5,308,181 | A * | 5/1994 | Hull | A01K 13/001 |
| | | | | 222/561 |
| 5,683,012 | A * | 11/1997 | Villaveces | A45F 5/02 |
| | | | | 222/175 |
| 5,927,548 | A * | 7/1999 | Villaveces | A45F 5/02 |
| | | | | 222/175 |
| 6,234,357 | B1 * | 5/2001 | Lewis | A45F 5/02 |
| | | | | 222/175 |

(Continued)

*Primary Examiner* — Jennifer C Chiang
*Assistant Examiner* — Bradley Oliver
(74) *Attorney, Agent, or Firm* — Whitaker Chalk Swindle & Schwartz PLLC; Charles D. Gunter, Jr.

(57) ABSTRACT

A personal dispensing system allows a user to dispense a viscous liquid, such as a disinfectant liquid gel. The dispenser includes a mounting clip which can be worn on the belt of a user. The dispenser has a front sidewall with openings which allow the viscous liquid to be dispensed onto a user's hands. The openings on the front sidewall of the container body and the viscosity of the liquid are selected so that the viscous liquid weeps out of the openings without dripping, or a hand pump can dispense the liquid. The front face of the device can also house a single horizontal roller or a number of roller balls for dispensing the viscous liquid.

4 Claims, 7 Drawing Sheets

(56) References Cited

U.S. PATENT DOCUMENTS

| | | | | |
|---|---|---|---|---|
| 7,988,020 | B2* | 8/2011 | Shoham | A61B 90/80 |
| | | | | 222/175 |
| 8,747,008 | B2* | 6/2014 | Geesbreght | A47K 5/12 |
| | | | | 401/131 |
| 8,876,422 | B2* | 11/2014 | Lim | A45D 34/04 |
| | | | | 401/188 R |
| 2004/0111071 | A1* | 6/2004 | Powers | A45D 34/00 |
| | | | | 604/310 |
| 2007/0003358 | A1* | 1/2007 | Futo | B05C 17/00 |
| | | | | 401/188 R |
| 2008/0017188 | A1* | 1/2008 | Pardonge | A61M 15/009 |
| | | | | 128/200.14 |
| 2013/0015211 | A1* | 1/2013 | Uxa, Jr. | A47K 5/1201 |
| | | | | 222/330 |
| 2013/0099929 | A1* | 4/2013 | Ophardt | A47K 5/1217 |
| | | | | 340/573.1 |
| 2014/0084028 | A1* | 3/2014 | Gunn | A45F 5/021 |
| | | | | 222/175 |
| 2014/0124531 | A1* | 5/2014 | Muderlak | A47K 5/1207 |
| | | | | 222/36 |
| 2014/0270897 | A1* | 9/2014 | Laurusonis | B05C 1/00 |
| | | | | 401/146 |
| 2015/0227705 | A1* | 8/2015 | Zaima | A61L 2/26 |
| | | | | 705/2 |

* cited by examiner

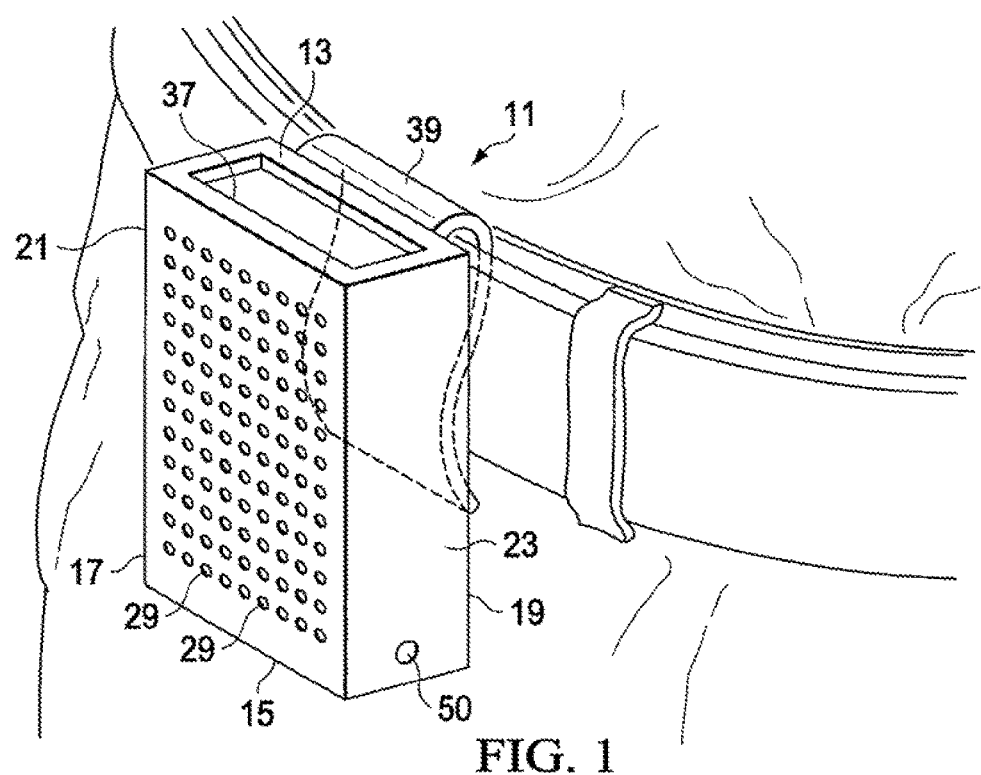
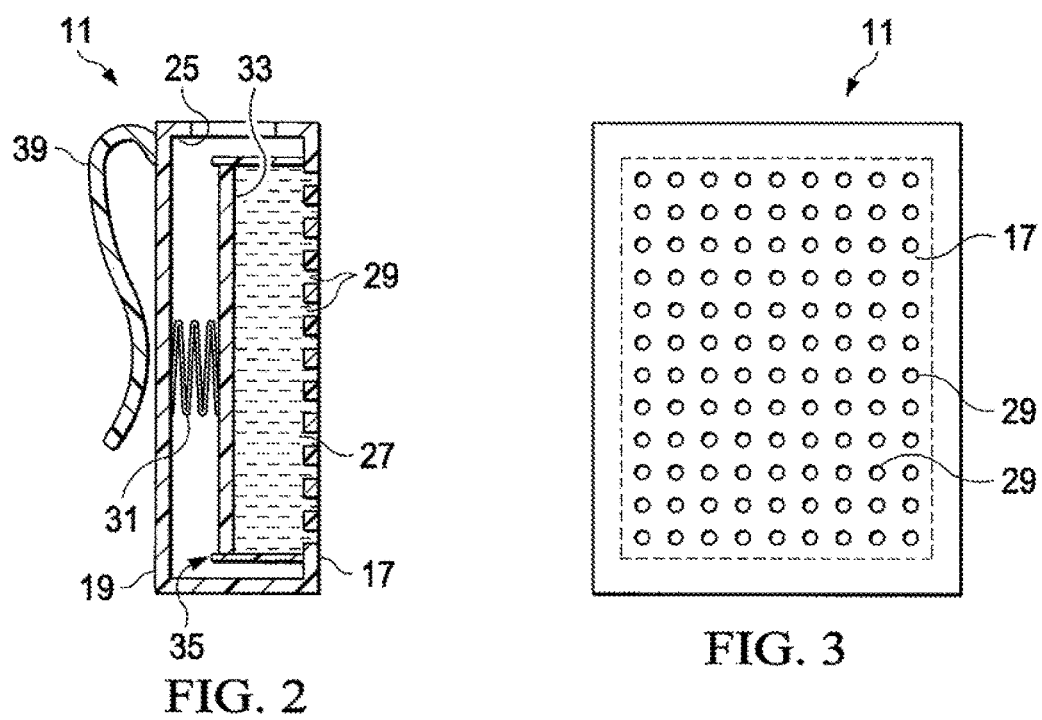

HAND SANITIZING DEVICE AND METHOD OF USE

CROSS REFERENCE TO RELATED APPLICATIONS

The present application is a divisional of earlier filed patent application Ser. No. 14/292,995, filed Jun. 2, 2014, which is a continuation-in-part of application Ser. No. 12/788,887, filed May 27, 2010, entitled "Hand Sanitizing Device and Method of Use", by the same inventors, which claimed priority from a provisional application, Ser. No. 61/181,724, filed May 28, 2009, entitled "Hand Sanitizing Device and Method of Use", by the same inventors.

BACKGROUND OF THE INVENTION

1. Field of the Invention

The present invention relates generally to a hand sterilizing or sanitizing device which can be worn by an individual user, or supported on a shelf or wall, and which can be self-energized to continuously dispense a predetermined quantity of a viscous sanitizing liquid, such as an antimicrobial gel, or which can be energized by a hand pump type of operation.

2. Description of the Prior Art

The uncontrolled spread of germs and viruses is recognized as a main cause of many illnesses. In recent years, a variety of hand sanitizing devices have entered the marketplace in an attempt to curtail the spread of these illness-causing organisms. The use of such devices is now commonplace in such environments as the medical community where workers such as emergency department and intensive care unit personnel are frequently exposed to such germs and viruses. Many professions and occupations require the use of hand cleaners or other skin care products on a frequent basis. For example, health care providers such as nurses must sanitize their hands after each patient. Often, the nurse must return to the nurses' station or to some other permanent dispenser location to perform this hand sanitizing, which can cause additional time pressure in an already busy environment.

It is imperative for the hands of medical workers to remain as germ free as possible, especially when treating patients. Hand sanitizers have proven to be a very valuable tool for reducing the incidence of infection. One disadvantage of the presently available hand sanitizer dispensers is the fact that it is often difficult and cumbersome for medical personnel that go from place to place to carry a bottle of hand sanitizer with them. Even where wall-mounted sanitizers are available, they are often empty when needed. In the case of, for example, an emergency department environment, personnel do not have the free time needed to seek out a full dispenser of sanitizer when confronted with one or more empty ones.

There are many other situations, in addition to the medical environment where a need exists for an improved hand sanitizer dispenser. As one typical example, the hands of an employee working in a printing, machining or other manufacturing type industry will often become soiled at the work station. The same can be said for workers involved in various sectors of the food industry. Frequent trips to the washroom for the purpose of hand cleaning are inefficient and unproductive. In other situations, such as in the case of a utility or similar outside worker, there may be no washroom facility available if the worker's hands become contaminated. In each of these types of situations, there is a need for a holder that conveniently attaches to a person to hold and dispense a predetermined quantity of hand sanitizer.

The present invention, therefore, has as one object to provide an improved dispenser which can be used to contain and dispense a predetermined viscous liquid, such as an anti-microbial gel.

Another object of the invention is to provide such a device which can be conveniently worn on the body or clothing of an individual user.

Another object of the invention is to provide such as device which is self-energizing so that it dispenses a convenient quantity of gel by weeping onto an exposed surface of the device, without dripping.

Another object is to provide such a device which features a hand pump type of operation for dispensing a quantity of gel.

Another object is to provide such a device which can be reloaded so as to be reusable from one shift to another.

Another object is to provide such a device which has a disposable cartridge so that it is able to be replaced at the beginning of each work shift.

Another object of the device of the invention is to have an indicator element which indicates when the gel/liquid content of the cartridge or device reservoir is near empty or empty.

SUMMARY OF THE INVENTION

The present invention recognizes and addresses the foregoing disadvantages, and others, of the prior art by providing an improved sanitizing product dispenser that is wearable by a worker.

It is a further object of the present invention to provide a wearable product dispenser that allows viscous liquid to be dispensed without removing the dispenser from a user's body.

It is a further object of the present invention to provide a wearable product dispenser that includes a removable cartridge type sanitizing element for facilitating reloading of the device with sanitizing agent, or which allows substitution of one type of sanitizer product for another.

It is a further object of the present invention that it may be used/activated by one hand.

The preferred viscous liquid dispenser of the invention can be used for dispensing a hand sanitizing composition. In one preferred form, the dispenser includes a container body having a top, a bottom, a front sidewall, a rear sidewall and opposing end walls which together define an initially closed interior. The container body has contained therein a selected quantity of a viscous liquid which is to be dispensed. The front sidewall of the container body is provided with a plurality of openings for dispensing the viscous liquid. A mounting element is located on the container body for mounting the dispenser on the body of a user. At least the diameter of the front sidewall openings and the viscosity of the liquid being dispensed are selected to provide certain predetermined flow characteristics for the dispenser. The flow characteristics are calculated to allow the viscous liquid to weep from the front sidewall openings of the container body without dripping, whereby a user's hand can be wiped across the front sidewall to dispense the viscous liquid onto the user's hand.

The mounting element can conveniently comprise a mounting clip which is worn on a user's belt or otherwise attached to the user's clothing. The preferred viscous liquid to be dispensed by the device of the invention is a viscous gel which is provided in the form of a replaceable cartridge which is received within the interior of the container body. The interior of the container body may also contain a biasing element, such as a coil spring, which exerts a force on an exposed surface of the replaceable cartridge to force the viscous liquid in the direction of the front sidewall openings of the dispenser. In its most preferred form, the viscous liquid comprises an anti-microbial hand sanitizing composition.

Instead of being self-energizing, the dispensing device can also have a hand pump type of operation. The hand pump can feature a simple up and down action which can be actuated with one hand.

In another form, the viscous liquid dispenser of the invention again includes a container body having a top, a bottom, a front sidewall, a rear sidewall and opposing end walls which together define an initially closed interior, the container body having contained therein a selected quantity of a viscous liquid. In this case, however, the front sidewall of the container body is provided with a centrally located opening and a gel pad is located within the container body interior, the gel pad having a front exposed surface which is received within the centrally located opening, whereby the front exposed surface can be accessed by a user for dispensing viscous liquid from the pad.

In this version of the invention, the gel pad has a plurality of openings provided on the front exposed surface thereof. At least the diameter of the openings and the viscosity of the liquid being dispensed are selected to provide certain predetermined flow characteristics for the dispenser, the flow characteristics being calculated to allow the viscous liquid to weep from the front exposed surface of the gel pad without dripping, whereby a user's hand can be wiped across the pad exposed surface to dispense the viscous liquid onto the user's hand.

In another form, the dispenser may utilize a roller ball larger in size but similar in function to an ink dispensing roller ball pen or to the rollers used in roll-on deodorants. The dispenser may also incorporate multiple roller balls. These multiple roller balls will pick up the viscous liquid/gel from the sanitizer cartridge and deliver them to the user's hand as the hand is swept across the face of the dispenser to thereby rotate the roller balls.

Additional objects, features and advantages will be apparent in the written description which follows.

BRIEF DESCRIPTION OF THE DRAWINGS

FIG. 1 is a perspective view of a hand sanitizing dispenser of the invention, the dispenser being mounted on a user's belt by means of a mounting clip.

FIG. 2 is a side, cross-sectional view of the dispenser of FIG. 1, showing the dispensing openings located in a front sidewall thereof.

FIG. 3 is front view of the dispenser of FIG. 2 showing the dispensing openings provided in the front sidewall thereof.

DETAILED DESCRIPTION OF THE INVENTION

Figure 4:
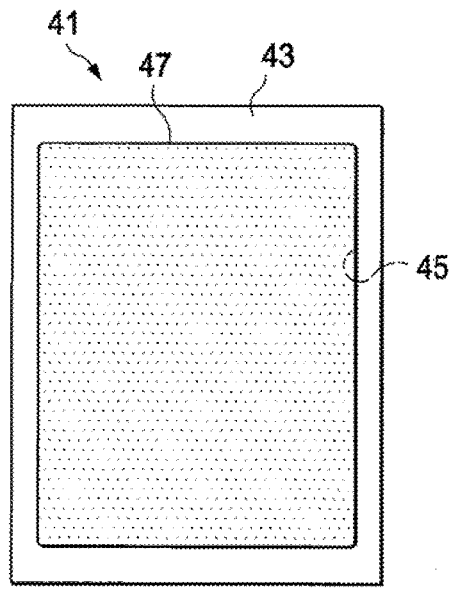
FIG. 4 is a front view of another version of the dispenser of the invention in which a centrally located opening provided in the front sidewall of the container body exposes a gel impregnated dispensing pad.

The embodiments herein and the various features and advantageous details thereof are explained more fully with reference to the non-limiting embodiments that are illustrated in the accompanying drawings and detailed in the following description. Descriptions of well-known components and processes and manufacturing techniques are omitted so as to not unnecessarily obscure the embodiments herein. The examples used herein are intended merely to facilitate an understanding of ways in which the invention herein may be practiced and to further enable those of skill in the art to practice the embodiments herein. Accordingly, the examples should not be construed as limiting the scope of the claimed invention.

With reference now to FIG. 1, there is shown a viscous liquid dispenser for dispensing a hand sanitizing composition, designated generally as 11. The dispenser 11 includes a container body having a top 13, a bottom 15, a front sidewall 17, a rear sidewall 19 and opposing ends walls 21, 23 which together define an initially closed interior (25 in FIG. 2). The container body has contained therein a selected quantity of a viscous liquid. In the case of the dispenser shown in FIGS. 1-3, the viscous liquid is in the form of a viscous gel 27. This gel will preferably be an anti-microbial gel composition having an alcohol content sufficient to provide the needed anti-microbial action. Alternatively, other known anti-microbial type agents such as gentian violet, methylene blue or like may be incorporated into the composition. A number of commercially available anti-microbial compositions are known, such as the Purell™ hand sanitizer product sold by the Dial Corporation. This product, or products of similar chemical composition may be suitable for purposes of the present invention, once the viscosity of the composition has been adjusted appropriately.

As can be seen in FIGS. 1-3, the front sidewall 17 of the container body is provided with a plurality of openings 29 for dispensing the viscous gel. At least the diameter of the front sidewall openings 29 and the viscosity of the liquid gel 27 being dispensed are selected to provide certain predetermined flow characteristics for the dispenser. These flow characteristics are calculated to allow the viscous liquid to weep from the front sidewall openings of the container body without dripping. In this manner, a user's hand can be wiped across the front sidewall to dispense the viscous liquid onto the user's hand. The viscous liquid then once again weeps through the wall openings 29 to the front sidewall surface for the next use.

The desired weeping action of the gel in the present device is somewhat similar to certain types of gel deodorants which are pushed up through top openings in the deodorant container by the user turning a knob on the base of the container. In the present device, the activation action may be provided by a biasing element, such as the coil spring 31 shown in FIG. 2. In the example shown in FIG. 2, the coil spring 31 acts upon a movable back panel 33 of a replaceable cartridge 35 which is located within the interior 25 of the dispenser. In this way, the cartridge can be removed through a top opening (37 in FIG. 1) of the dispenser when empty. It is envisioned that the cartridge will contain sufficient viscous gel to allow use through one work shift, in the case of, for example, hospital workers. Preferably, an indicator, such as the viewing port 50 in FIG. 1, is included to allow a user to monitor the level of gel remaining in the cartridge. The level indicator might take a variety of forms, such as incorporating an electrically actuated LED indicator.

As shown in FIGS. 1 and 2, the dispenser is conveniently provided with a mounting element, such as the mounting clip 39 which allows the device to be supported on a user's belt or other item of clothing. The portable nature of the device insures that the hand sanitizer is always conveniently available without having to search out a more permanent installation.

A number of variables may enter into the ultimate design characteristics of the viscous liquid (gel) used for the purposes of the invention. Obviously the diameter of the openings 29 and the viscosity of the gel itself will be critical to the proper functioning of the device. Other factors, such as the surface tension on the exposed front wall 17 of the dispenser as the user's hand passes over the surface must be taken into account.

Figure 5:
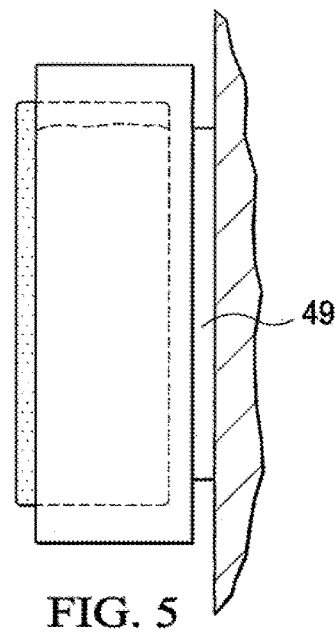
FIG. 5 is a side view of the dispenser of FIG. 4.
Figure 6:
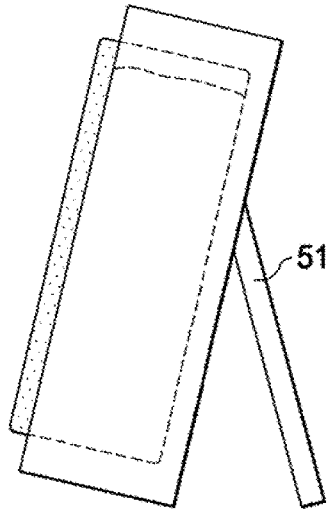
FIG. 6 is a side view of a third form of the dispenser of the invention in which the dispenser is provided with a stand or wall mount.

FIGS. 4-6 illustrate another form of the invention in which the dispenser body 41 has a front sidewall 43 which is provided with a centrally located opening 45. A gel pad 47 is located within the container body interior. The gel pad has a front exposed surface which is received within the centrally located opening 45, whereby the front exposed surface can be accessed by a user for dispensing viscous liquid from the pad. In the case of the dispenser shown in FIGS. 4-6, the gel pad 47 has a plurality of openings provided on the front exposed surface thereof. Once again, at least the diameter of the openings and the viscosity of the liquid gel being dispensed are selected to provide certain predetermined flow characteristics for the dispenser. The flow characteristics are calculated to allow the viscous liquid to weep from the front exposed surface of the gel pad without dripping, whereby a user's hand can be wiped across the pad exposed surface to dispense the viscous liquid onto the user's hand.

The pad 47 can once again be acted upon by a biasing element, such as the coil spring shown in FIG. 2. A mounting clip (49 in FIG. 5) provides a convenient means for attaching the device to the user's clothing. As in the case of the gel cartridge shown in FIGS. 1-3, the gel pad (47 in FIG. 4) is preferably supplied as a replaceable element which is received within the interior of the container body of the dispenser, whereby the container body can be reused by replacing the gel pad.

It is also possible that a porous pad could simply be located in the centrally located opening 45 with a gel reservoir or cartridge being located behind the porous pad. Once again, the user would simply wipe the exposed front surface of the porous pad to dispense the gel.

While the device is preferably worn on a person's clothing, such as attached to a belt, it will be understood that the device could be provided with another type of support, such as the stand 51 shown in FIG. 6. This would allow the device to be supported on a shelf or wall mounted for more permanent type installations.

Figure 7:
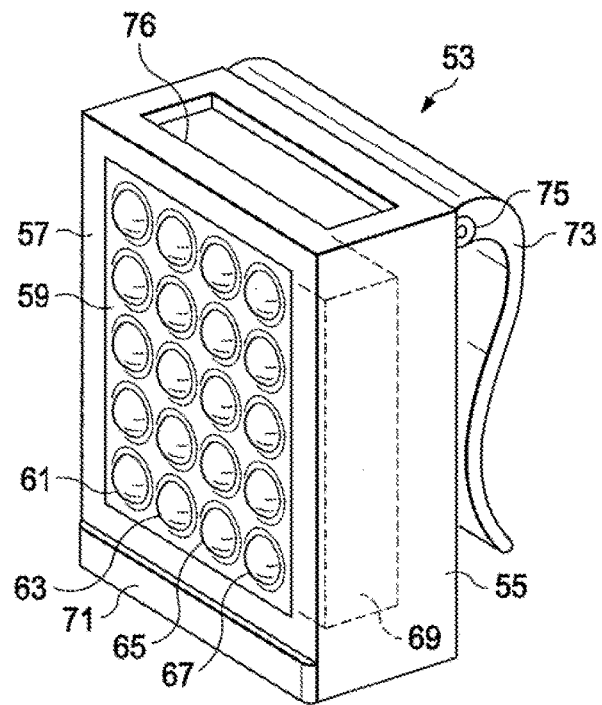
FIG. 7 is a perspective view of yet another form of the dispenser of the invention in which the viscous liquid/gel is dispensed by a plurality of roller balls located on the front face of the device.
Figure 8:
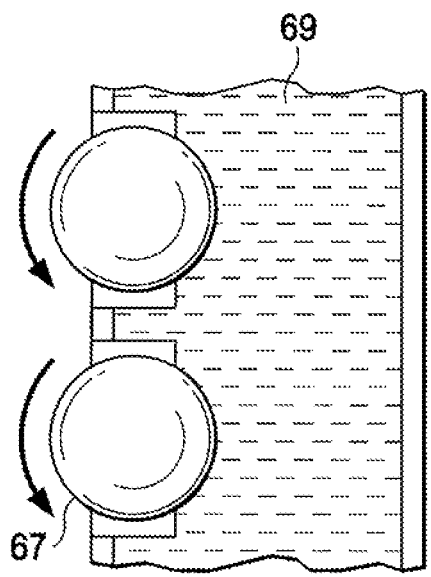
FIG. 8 is a side, partial cross-sectional view of the device of FIG. 7 showing the movement of the roller balls on the front exposed region of the dispenser body.

FIG. 7 shows another form of the device of the invention, designated generally as 53. In the case of the device 53, the dispenser body 55 has a front sidewall 57 which is provided with a centrally located exposed face region 59. The exposed face region 59 has mounted thereon a plurality of rows of roller balls, such as balls 61, 63, 65, 67 in FIG. 7. The balls are similar in design to those used in ink dispensing roller ball pens, but are larger in diameter. They are also similar to the rollers used in roll-on deodorants. They are mounted so as to be freely rotatable within associated openings provided in the exposed face region 59 of the dispenser body (see FIG. 8). Once again, a gel cartridge (shown in dotted lines as 69 in FIG. 7) is located within the container body interior and is used to supply viscous liquid/gel to the roller balls. The cartridge can be removed through a top opening or lid 76 in order to replace the gel cartridge at the beginning of each work shift.

In order to use this version of the device, a user merely sweeps a hand across the exposed face region 59. This action causes the balls to rotate and pick up gel from the gel cartridge 69, thereby applying the gel to the user's hand. The container body may also be provided with a drip shield 71 to catch any excess gel. Further, the container body may be provided with a suitable mounting device, such as a clip to be worn on a user's belt (73 in FIG. 7). In the example of FIG. 7, the clip mount 73 is provided with a pivotal attachment point 75 to provide a "pivoting" action to the box in the same way that certain cell phone holders rotate about a pivot point on a user's belt.

Figure 9:
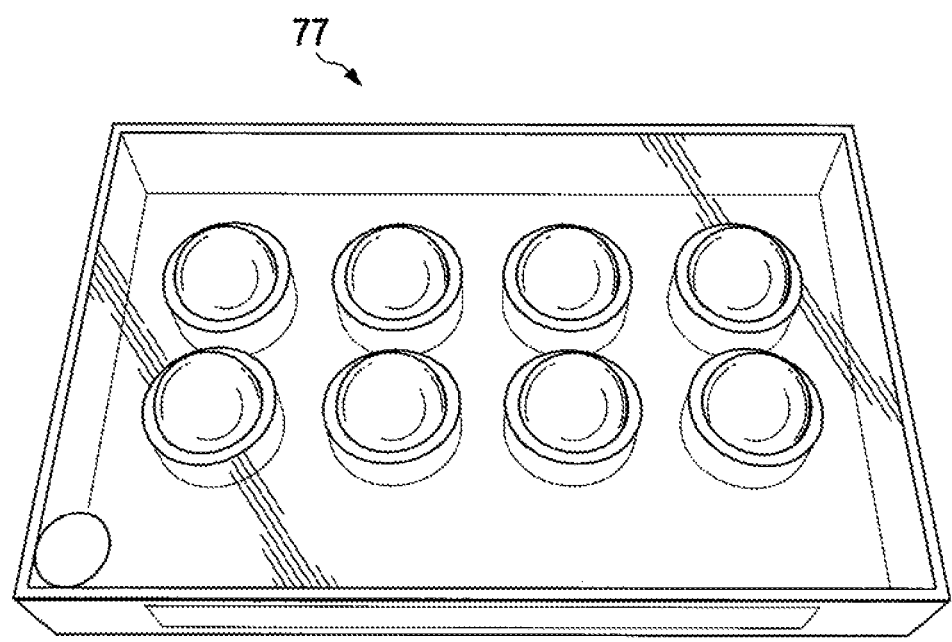
FIG. 9 is a front perspective view of a roller ball container body similar to FIG. 7.

FIG. 9 is another view of the dispenser body of the roll-on version of the invention (designated generally as 77) showing two rows of rollers mounted in a container body.

Figure 10:
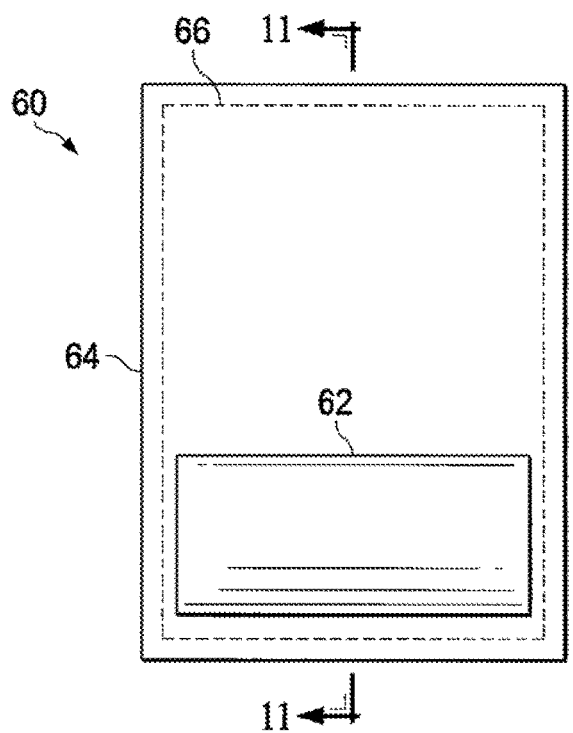
FIG. 10 is a front view of another type dispenser of the invention which utilizes a gel reservoir and a single roller.
Figure 11:
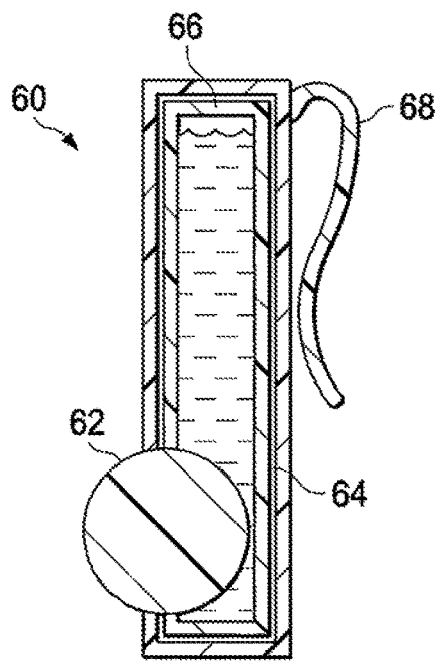
FIG. 11 is a side view of the roller dispenser of FIG. 10.

FIGS. 10 and 11 illustrate another roller type dispenser, designated generally as 60. In this version of the roller dispenser device, only a single horizontal roller 62 is used. The roller sits in a trough region at the bottom of the dispenser body 64. A quantity of liquid gel is maintained in a reservoir region 66 of the body. The gel is dispensed when a user passes a hand across the roller, causing it to rotate about a horizontal axis and pick up liquid gel from the gel reservoir. The gel reservoir could contain a cartridge, as has been explained with reference to certain of the earlier versions of the invention, or could simply be an initially empty cavity which could be re-filled from a source of liquid gel, such as at the beginning of each hospital shift. The dispenser body 64 could also be provided with a belt clip 68 which could be used to attach the dispenser body to a user's belt or other convenient position on the user's clothing.

Figure 12:
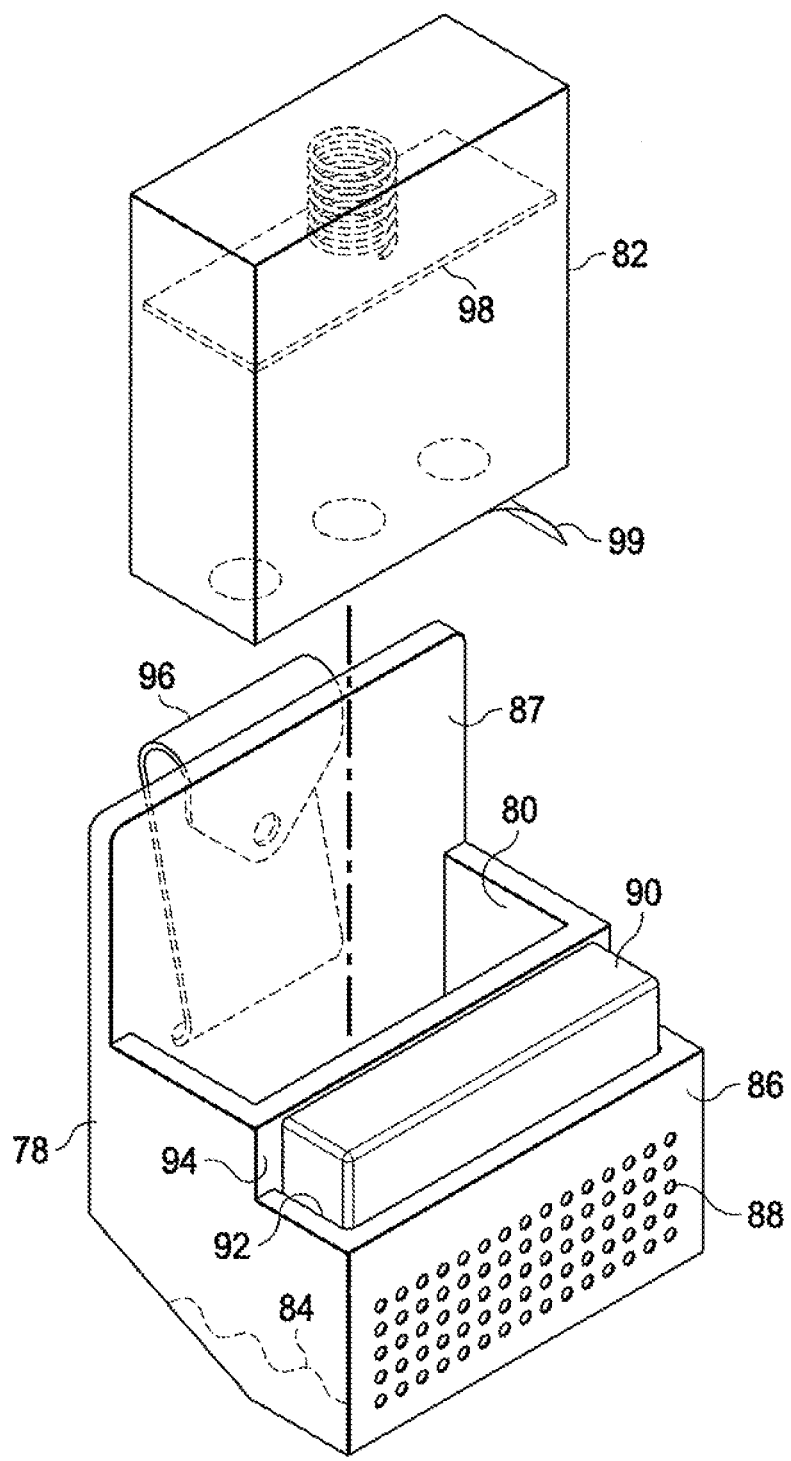
FIG. 12 is a view of another type of dispenser which features a hand pump type operation by means of an up and down pump element, the gel cartridge being shown in exploded fashion.
Figure 13:
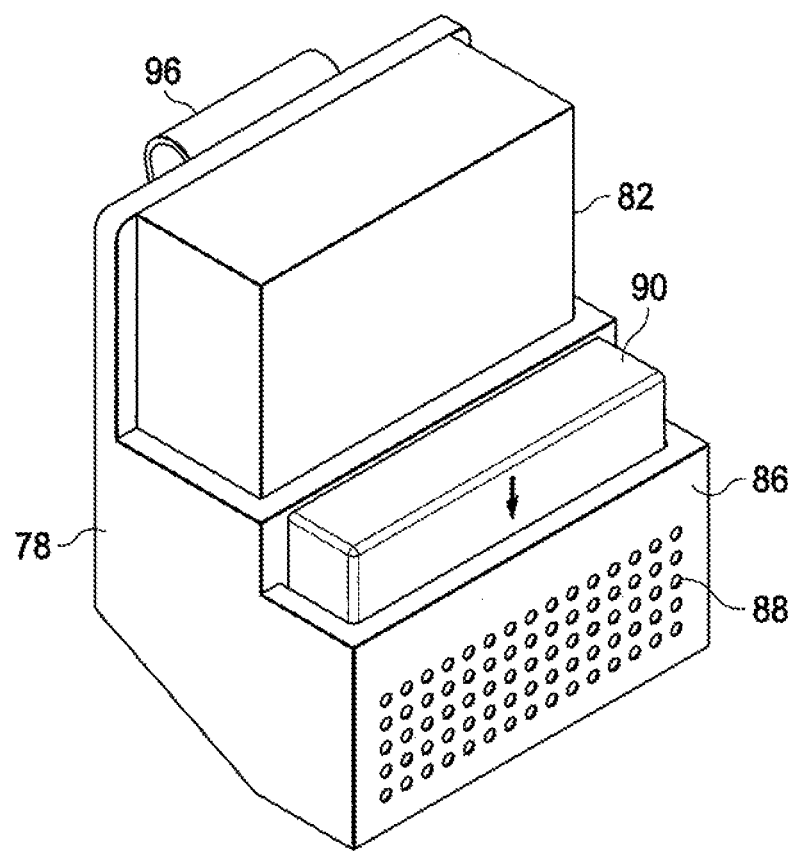
FIG. 13 is a view similar to FIG. 10 with the gel cartridge being shown in place in a receptacle opening on the body of the dispenser.

FIGS. 12-13 show another version of the dispensing device of the invention, similar to that shown in FIGS. 1-3. In this version of the invention, however, the dispenser body 78 has an upwardly facing receptacle opening 80 for receiving a gel cartridge 82. The cartridge 82 discharges gel downwardly into a reservoir region (indicated generally at 84 in FIG. 12). This could be accomplished in any of a number of ways. For example, the cartridge 82 could have an internal backing plate which is spring biased by a coil spring 98. The cartridge could have a lower opening which is initially sealed by a pull off strip 99. The user would pull off the strip prior to inserting the cartridge into the receptacle opening 80.

The dispenser body is a tiered structure which again has a front wall 86 and a rear wall 87. In this case, the front and rear walls are separated by an intermediate wall 94. The front wall has a plurality of openings 88 which are appropriately sized to dispense the gel from the reservoir 84. A hand pump element 90 is located in an upwardly facing opening 92 on the dispenser body between the front wall 86 and the intermediate wall 94. The user dispenses gel through the front wall openings 88 by simply pushing downwardly on the hand pump element 90, as indicated by the arrow in FIG. 13. The device can again be held on the body of the user, as with a belt clip 96.

Note that the gel cartridge 82 can be provided in various sizes or lengths since it can extend from the reservoir opening 80, if necessary. The larger size cartridge could be provided to accommodate longer hospital shifts, or the like. FIG. 13 shows a standard sized cartridge in place in the cartridge receptacle opening 80.

Figure 14:
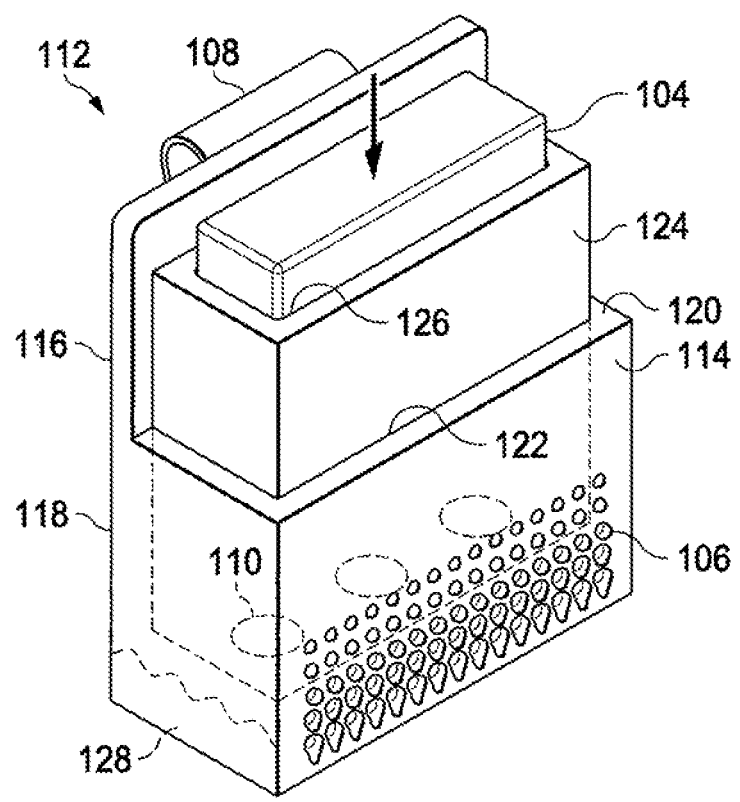
FIG. 14 is a view of another hand pump type dispenser in which a replaceable cartridge itself incorporates the hand pump mechanism which is used to dispense gel from the device.

FIG. 14 shows another form of the hand pump type dispenser 112. The dispenser 112 has a dispenser body with a front wall 114, a rear wall 116 and opposing sidewalls 118, 120, which together define a receptacle opening 122 for receiving a hand sanitizing cartridge 124 which itself contains a viscous sanitizing liquid. In the example of the device shown in FIG. 14, the cartridge 124 itself incorporates a pump element 104. The pump element moves downwardly within a track opening 126 provided in the cartridge body. Similar to the cartridge 82 shown in FIG. 12, the cartridge 102 could have a perforated bottom with at least one bottom opening (shown in dotted lines as 110 in FIG. 14) which would be accessed by pulling a pull strip (such as strip 99 in FIG. 12) prior to inserting the cartridge into its receptacle on the dispenser body. Alternatively, the openings 106 in the front face of the dispenser body could also be initially covered with a pull off strip (not shown).

A reservoir region 128 is located in the bottom region of the dispenser body. The openings 110 in the cartridge body would supply viscous sanitizing liquid to the reservoir region 128. Liquid gel would be dispensed from the openings 106 on the dispenser body by the user pushing downwardly on the pump element 104. The cartridge could assume any convenient form for dispensing liquid gel into the reservoir region 128 adjacent the openings 106. The pump element could simply work by having a given stroke length with the user pushing downwardly to dispense liquid gel. In such case, a new cartridge would be needed when the bottom of the stroke length was met and all of the liquid gel had been dispensed from the cartridge. This version of the dispenser body is also equipped with a belt clip 108.

An invention has been provided with several advantages. The device is simple in design and economical to manufacture. The chemical makeup of the viscous liquid compositions can be based upon readily available anti-microbial compositions which are presently available in the marketplace. The portable nature of the device insures that the hand sanitizer is always conveniently available for use. The self-energizing nature of the device insures that the anti-microbial type agent is always available by swiping the hand across the active surface of the device. In another version, a simple hand pump can be operated with one hand to dispense gel sanitizer. One or more roller balls can also conveniently be used to dispense the santizer, such as a commonly available liquid gel sanitizer.

While the invention has been shown in several of its forms, it is not thus limited but is susceptible to various changes and modifications without departing from the spirit thereof.

What is claimed is:

1. A liquid dispenser for dispensing a hand sanitizing composition, the dispenser comprising:

a dispenser body having a front wall and a rear wall and opposing sidewalls which together define a receptacle opening for receiving a hand sanitizing cartridge which itself contains a sanitizing liquid, the front wall of the dispenser body being provided with a plurality of openings for dispensing the sanitizing liquid, the sanitizing cartridge having a bottom opening for supplying viscous sanitizing liquid to a reservoir region located behind the front wall adjacent the front wall openings in the dispenser body;

wherein the cartridge itself incorporates a hand pump element which moves downwardly within a track opening provided in the cartridge body to thereby force sanitizing liquid from the reservoir region and outwardly through the openings in the front wall and into the user's hand; and a mounting element located on the container body for mounting the dispenser on the body of the user.

2. The dispenser of claim 1, wherein the sanitizing liquid is a liquid disinfectant gel.

3. The dispenser of claim 2, wherein, the cartridge has a perforated bottom with at least one bottom opening which is initially covered by a pull strip, the pull strip being removable prior to inserting the cartridge into the receptacle on the dispenser body, whereby downward movement of the hand pump element forces sanitizing liquid from the reservoir region and outwardly through the openings in the front wall and into the user's hand.

4. The dispenser of claim 3, wherein the hand pump element incorporated in the cartridge has a given stroke length determined between a start point and an end point, whereby when the user pushes downwardly to dispense liquid gel, the user receives an indication that a new cartridge is needed when the end point of the stroke length is met and all of the liquid gel has been dispensed from the cartridge.

* * * * *